United States Patent
Fortin

(10) Patent No.: US 11,478,443 B2
(45) Date of Patent: *Oct. 25, 2022

(54) POLYUNSATURATED FATTY ACID MONOGLYCERIDES, COMPOSITIONS, METHODS AND USES THEREOF

(71) Applicant: SCF PHARMA INC., Sainte-Luce (CA)

(72) Inventor: Samuel C. Fortin, Sainte-Luce (CA)

(73) Assignee: SCF PHARMA INC., Sainte-Luce (CA)

( * ) Notice: Subject to any disclaimer, the term of this patent is extended or adjusted under 35 U.S.C. 154(b) by 305 days.

This patent is subject to a terminal disclaimer.

(21) Appl. No.: 16/910,055

(22) Filed: Jun. 23, 2020

(65) Prior Publication Data

US 2020/0316007 A1 Oct. 8, 2020

Related U.S. Application Data

(63) Continuation of application No. 16/517,607, filed on Jul. 21, 2019, now Pat. No. 10,716,776, which is a continuation-in-part of application No. PCT/CA2019/050139, filed on Feb. 4, 2019.

(60) Provisional application No. 62/627,244, filed on Feb. 7, 2018.

(51) Int. Cl.

| A61K 36/00 | (2006.01) |
| --- | --- |
| A61K 31/232 | (2006.01) |
| A61K 31/05 | (2006.01) |
| A61K 31/192 | (2006.01) |
| A61K 31/352 | (2006.01) |
| A61K 35/60 | (2006.01) |
| A61K 36/185 | (2006.01) |

(52) U.S. Cl.
CPC ............ *A61K 31/232* (2013.01); *A61K 31/05* (2013.01); *A61K 31/192* (2013.01); *A61K 31/352* (2013.01); *A61K 35/60* (2013.01); *A61K 36/185* (2013.01)

(58) Field of Classification Search
None
See application file for complete search history.

(56) References Cited

U.S. PATENT DOCUMENTS

| 6,180,671 | B1 | 1/2001 | Freedman et al. |
| 6,552,081 | B1 | 4/2003 | Freedman et al. |
| 7,138,431 | B1 | 11/2006 | Chilton |
| 7,981,915 | B2 | 7/2011 | Freedman |
| 8,119,690 | B2 | 2/2012 | Fortin |
| 8,198,324 | B2 | 6/2012 | Fortin |
| 8,222,295 | B2 | 7/2012 | Fortin |
| 8,329,747 | B2 | 12/2012 | Fortin |
| 8,722,737 | B2 | 5/2014 | Fortin |
| 8,816,110 | B2 | 8/2014 | Fortin |
| 9,101,563 | B2 | 8/2015 | Fortin |
| 9,233,915 | B2 | 1/2016 | Fortin |
| 9,447,020 | B2 | 9/2016 | Fortin |
| 9,480,660 | B2 | 11/2016 | Fortin |
| 9,670,133 | B2 | 6/2017 | Koch et al. |
| 9,925,165 | B2 | 3/2018 | Fortin |
| 10,716,776 | B2 | 7/2020 | Fortin |
| 2002/0188024 | A1 | 12/2002 | Chilton et al. |
| 2004/0214799 | A1 | 10/2004 | Mukai et al. |
| 2006/0121583 | A1 | 6/2006 | Lassalle et al. |
| 2009/0291102 | A1 | 11/2009 | Fortin |
| 2009/0292019 | A1 | 11/2009 | Fortin |
| 2010/0160261 | A1 | 6/2010 | Fortin |
| 2010/0196496 | A1 | 8/2010 | Fortin |
| 2012/0213872 | A1 | 8/2012 | Fortin |
| 2012/0251582 | A1 | 10/2012 | Fortin |
| 2013/0059911 | A1 | 3/2013 | Fortin |
| 2015/0119591 | A1 | 4/2015 | Fortin |
| 2015/0343071 | A1 | 12/2015 | Vangara et al. |
| 2017/0049830 | A1 | 2/2017 | Raderman |
| 2018/0078504 | A1 | 3/2018 | Sacks et al. |
| 2018/0264121 | A1 | 9/2018 | Donaduzzi et al. |
| 2019/0133992 | A1 | 5/2019 | Shaaban |
| 2019/0231833 | A1 | 8/2019 | Garti et al. |
| 2019/0314326 | A1 | 10/2019 | Garti et al. |
| 2019/0374502 | A1 | 12/2019 | Jha |
| 2020/0121606 | A1 | 4/2020 | Sacks et al. |

FOREIGN PATENT DOCUMENTS

| CA | 2538382 | 3/2005 |
| CA | 2599473 | 9/2006 |
| EP | 1352648 | 10/2003 |

(Continued)

OTHER PUBLICATIONS

Cockbain et al., "Omega-3 polyunsaturated fatty acids for the treatment and prevention of colorectal cancer", Gut 2012; 61: 135-149 (Published Online First: Apr. 13, 2011).
Barry et al., "Anticancer Agents. IV. 1 a,b The antitumor Activity of Some 1,4- and 1,5-(Bisthiosemicarbazones) and of Related Heterocycles" Journal of Meidcinal Chemistry, 1970, vol. 13, No. 3 (Received Sep. 10, 1968).
Liang et al., "Effect of dietary omega-3 fatty acids on tumor-associated macrophages and prostate cancer progression". Prostate, Oct. 2016, 76(14): 1293-1302.
Newell et al., "A Critical Review on the Effect of Docosahexaenoic Acid (DHA) on Cancer Cell Cycle Progression", Int J Mol Sci. Aug. 2017; 18(8): 1784.
Ramsaywack et al., "Synthesis and Surface Investigations of N-Substitued 2,5-Dithio-7-azabicyclo[2.2.1]heptanes on Gold Surfaces", J. Phys. Chem. C Mar. 16, 2012, 116, 7886-7896.

(Continued)

*Primary Examiner* — Michael V Meller
(74) *Attorney, Agent, or Firm* — Bereskin & Parr LLP/S.E.N.C.R.L., s.r.l.

(57) ABSTRACT

There are provided various compositions comprising monoglyceride(s), diglyceride(s) and cannabinoid(s). These compositions can be useful for increasing the life span of a subject; for increasing the disability-free life expectancy, for slowing down the ageing process of a subject; for increasing the mitochondrial OXPHOS of a subject; for decreasing the mitochondrial LEAK of a subject; for increasing the mitochondrial RCR or COUPLING EFFICIENCY of a subject; and for optimizing the mitochondrial functions of a subject.

1 Claim, 13 Drawing Sheets

(56) References Cited

FOREIGN PATENT DOCUMENTS

| | | |
|---|---|---|
| JP | 2010132631 | 6/2010 |
| WO | 2002064166 | 8/2002 |
| WO | 2002089787 | 11/2002 |
| WO | 2002096408 | 12/2002 |
| WO | 2004000333 | 12/2003 |
| WO | 2004024136 | 3/2004 |
| WO | 2004064716 | 8/2004 |
| WO | 2006117668 | 11/2006 |
| WO | 2008036353 | 3/2008 |
| WO | 2015063041 | 5/2015 |
| WO | 2016066460 | 5/2016 |
| WO | 2017216362 | 12/2017 |
| WO | 2019234728 | 12/2019 |
| WO | 2020028991 | 2/2020 |
| WO | 2020044118 | 3/2020 |
| WO | 2021022378 | 2/2021 |

OTHER PUBLICATIONS

Shao et al., "Structural characterization of self-assemblies of new omega-3 lipids: docosahexaenoic acid and docosapentaenoic acid monoglycerides", Phys. Chem. Phys., Aug. 31, 2018, 20, 23928.
Vairoletti et al., "Synthesis of bicyclic 1,4-thiazepines as novel anti-Trypanosoma brucei brucei agents", Med. Chem. Commun., Jun. 11, 2019, 10, 1481.
Zgair et al., "Oral administration of cannabis with lipids leads to high levels of cannabinoids in the intestinal lymphatic system and prominent immunomodulation", Scientific Reports, 7:14542, Published online: Nov. 6, 2017.
Zhdanko et al., "One-step synthesis of N-acetylcysteine and glutathione derivatives using the Ugi reaction", Tetrahedron 65 (Apr. 17, 2009) 4692-4702.
Egil Fosslien, "Review: Mitochondrial Meidine—Molecular Pathology of Defective Oxidative Phosphorylation", Annals of Clinical & Laboratory Science, vol. 31, No. 1, 2001, pp. 25-67.
Marsicano et al., "Neuroprotective properties of cannabinoids against oxidative stress: role of the cannabinoid receptor CB1", Journal of Neurochemistry, vol. 80, Issue 3, Jan. 21, 2002.
Abstract of Herrera et al., "The CB2 cannabinoid receptor signals apoptosis via ceramide-dependent activation of the mitochondrial intrinsic pathway", Experimental Cell Research, vol. 312, Issue 11, Jul. 1, 2006, pp. 2121-2131.
Abstract of Athanasiou et al., "Cannabinoid receptor agonists are mitochondrial inhibitors: A unified hypothesis of how cannabinoids modulate mitochondrial function and induce cell death", Biomedical and Biophysical Research Communications, vol. 364, Issue 1, Dec. 7, 2007, pp. 131-137.
Tedesco et al., "Cannabinoid Type 1 Receptor Blockade Promotes Mitochondrial Biogenesis Through Endothelial Nitric Oxide Synthase Expression in White Adipocytes", Diabetes, vol. 57, Aug. 2008.
Alcock et al., "Fatty acids from diet and microbiota regulate energy metabolism" [version 1; referees: 2 approved], F1000 Research 2015, F(F1000 Faculty Rev):738 / Last updated: Sep. 10, 2015.
Constantini et al., "Impact of Omega-3 Fatty Acids on the Gut Microbiota", Int. J. Mol. Sci. Dec. 7, 2017, 18, 2645.
Khaddaj-Mallat et al., "Novel n-3 PUFA monoacylglycerides of pharmacological and medicinal interest: Anti-inflammatory and anti-proliferative effects", European Journal of Pharmacology 792 (Oct. 31, 2016) 70-77.
Piazzi et al., "Eicosapentaenoic acid free fatty acid prevents and suppresses colonic neoplasia in colitis-associated colorectal cancer acting on Notch signaling and gut microbiota", Int. J. Cancer: 135, 2004-2013 (Mar. 19, 2014).
Png et al., "Mucolytic Bacteria With Increased Prevalence in IBD Mucosa Augment In Vitro utilization of Mucin by Other Bacteria", Am J. Gastroenterol 2020; 105:2420-2428 (published online Jul. 20, 2010).

Davani-Davari et al., "Prebiotics: Definition, Types, Sources, Mechanisms, and Clinical Application", Foods 2019, 8, 92 (Published Mar. 9, 2019).
Turmeric—The Genus Curcuma, Edited by P.N. Ravindran et al., Jul. 24, 2006.
Akoh, "Lipase-Catalyzed Synthesis or Partial Glyceride", Biotechnology Letters, vol. 15, No. 9 (Sep. 1993) pp. 949-954.
Ando et al., "Reinvestigation of Positional Distribution of Fatty Acids in Docosahexaenoic Acid-Rich Fish Oil Triacyl-sn-glycerols", Lipids, vol. 35, No. 5 (2000) pp. 579-582.
Beharry et al., "Long-term docosahexaenoic acid therapy in a congenic murine model of cystic fibrosis", Am J Physiol Gastrointest Liver Physiol 292:G839-G848, 2007 First Published Nov. 9, 2006.
Chau et al., "Monoglyceride and diglyceride lipases from human platelet microsomes", Biochimica et Biophysica Acta, 963 (Jun. 1988) 436-444.
Duvoix et al., "Chemopreventive and therapeutic effects of curcumin", Cancer Letters 223 (2005) 181-190.
English Abstract of JP02131418, "Comparison of enhanced and routine methods for measuring ambient low-level sulfur dioxide", published on May 21, 1990.
English Abstract of JP7149786, "Glyceroglycolipid and Carcinogenic Promoter Inhibitor" published on Jun. 13, 1995.
English Abstract of JP62077319, "Anticancer pharmaceuticals containing eicosapentaenoic acid, its esters, or glycerides", published on Apr. 9, 1987.
English Abstract of JP2000044588, "Novel monoacylglycosyl monoacylglycerols for surfactants", published on Feb. 15, 2000.
Li et al., "Biosynthesis of Docosahexaenoate-Containing Glycrolipid Molecular Species in the Retina", Journal of Molecular Neuroscience, vol. 16, Nov. 1, 2001.
Freedman et al., "Fatty acids in cystic fibrosis", Current Opinion in Pulmonary Medicine 2000, 6:530-532.
Kafrawy et al., "Docosahexaenoic acid in phosphatidylcholine mediates cytotoxicity more effectively than other ω-3 and ω-6 fatty acids", Cancer Letters 132 (May 19, 1998) 23-29.
Kawashima et al., "Inhibition of Rat Liver Microsomal Desaturases by Curcumin and Related Compounds", Biosci. Biotech Biochem 60 (1), 108-110, 1996.
Kawashima et al., "Nicardipine and Nifedipine Inhibit Fatty Acid Desaturases in Rat Liver Microsomes", Biosci. Biotech. Biochem., 60 (10), 1672-1676, 1996.
Kawashima et al., "Inhibitory effects of alkyl and its derivatives on fatty acid desaturation", Biochimica et Biophysica Acta 1299 (1996) 34-38.
Kawashima et al., "Enzymatic Synthesis of High-Purity Structured Lipids with Caprylic Acid at 1,3-Positions and Polyunsaturated Fatty Acid at 2-Position", JAOCS, vol. 78, No. 6 (2001).
Martin et al., "The safety and efficacy of oral docosahexaenoic acid supplementation for the treatment of primary sclerosing cholangitis—a pilot study", Aliment Pharmacol Ther 2012; 35: 255-265.
Monks et al., "Feasibility of a High-Flux Anticancer Drug Screen Using a Diverse Panel of Cultured Human Tumor Cell Lines", Articles, vol. 83, No. 11, Jun. 5, 1991.
Abstract of Myrdal et al., "Solubilization of Drugs in Aqueous Media", Encyclopedia of Pharmaceutical Technology, published on Oct. 2, 2006.
Nakano et al., "Inhibitory Effects of Capsaicinoids on Fatty Acid Desaturation in a Rat Liver Cell Line", Biosci. Biotechnol. Biochem., 65 (8), 1859-1863, Mar. 29, 2001.
Ohta et al., Action of a New Mammalian DNA Polymerase Inhibitor, Sulfoquinovosyldiacylglycerol, Biol. Pharm. Bull. 22 (2) 111-116, Feb. 1999.
Pacetti et al., "High performance liquid chormatography-tandem mass spectometry of phospholipid molecular species in eggs from hen fed diets enriched in seal blubber oil", Journal of Chromatography A, 1097 (Aug. 30, 2005) 66-73.
Abstract of Rohan et al., "Dietary factors and survival from breast cancer", Nutr Cancer, 1993;20(2):167-177.
Rose et al., "Omega-3 fatty acids as cancer chemopreventive agents", Pharmacology & Therapeutics 83 (1999) 217-244.

(56) References Cited

OTHER PUBLICATIONS

Rosu et al., "Enzymatic synthesis of glycerides from DHA-enriched PUFA ethyl ester by glycerolysis under vacuum", Journal of Molecular Catalysis B: Enzymatic 4 (1998) 191-198.

Rubinstein et al., "Comparison of In Vitro Anticancer-Drug-Screening Data Generated With a Tetrazolium Assay Versus a Protein Assay Against a Diverse Panel of Human Tumor Cell Lines", Articles, vol. 82, No. 13, Jul. 4, 1990.

Schaaf et al., "Polyunsaturated Monoglycerides and a Pregnadiene in Defensive Glands of the Water Beetle *Agabus affinis*", Lipids, vol. 35, No. 5 (2000).

Shimizu et al., "Sesamin is a Potent and Specific Inhibitor of Δ5 Desaturase in Polyunsaturated Fatty Acid Biosynthesis", Lipids, vol. 26, No. 7 (1991).

Skehan et al., "New Colorimetric Cytotoxicity Assay for Anticancer-Drug Screening", Articles, vol. 82, No. 13, Jul. 4, 1990.

Tanaka et al., "Preparative Separation of Acylglycerol by Centrifugal Partition Chromatography (CPC)", Thermochimica (1990).

Vandevoorde et al., "Influence of the degree of unsaturation of the acyl side chain upon the interaction of analogues of 1-arachdonoylglycerol with monoacylglycerol lipase and fatty acid amid hydrolase", Biochemical and Biophysical Research Communication 337 (Sep. 13, 2005) 104-109.

Watanabe et al., "Chemical signals involved in larval metamorphosis in Hydroides ezoensis (Serpulidae; Polychaeta). Part II: Isolation and identification of a new monoacyl glycerol from adult tube clumps as a metamorphosis-inducing substance", J Mar Biotechnol (1998) 6:11-15.

Watanabe et al., "n-3 Polyunsaturated fatty acid (PUFA) deficiency elevates and n-3 PUFA enrichment reduces brain 2-arachidonoylglycerol level in mice", Prostaglandins, Leukotrienes and Essential Fatty Acids 69 (Mar. 20, 2003) 51-59.

Yamane et al., "Multiple Intensified Performance of an Enzyme-Catalyzed Reaction in Organic Medium", Analysis New York Academy Sciences (1988).

Zerouga et al., "Synthesis of a novel phosphatidylcholine conjugated to docosahexaenoic acid and methotrexate that inhibits cell proliferation", Anti-Cancer Drugs 2002, pp. 301-311.

Debora Cutuli, "Functional and Structural Benefits Induced by Omega-3 Polyunsaturated Fatty Acids During Agin", Current Neuropharmacology, 2017, 15, 534-542.

English Abstract of JP2010132631A, "Composition Having Inverse Agonist and Antagonist Activities of Cannabicoid Receptor", published on Jun. 17, 2010.

Flachs et al., "Polyunsaturated fatty acids of marine origin upregulate mitochondrial biogenesis and induce β-oxidation in white fat", Diabetologia (Oct. 5, 2005) 48:2365-2375.

Herbst et al., "Omega-3 supplementation alters mitochondrial membrane composition and respiration kinetics in human skeletal muscle", J. Physiol. 592.6 (Jan. 6, 2014) pp. 1341-1352.

Johnson et al., "Eicosapentaenoic acid but not docosahexaenoic acid restores skeletal muscle mitochondrial oxidative capacity in old mide", Aging Cell (2015) 14, pp. 734-743.

Morin et al., "Docosapentaenoic acid monoacylglyceride reduces inflammation and vascular remodeling in experimental pulmonary hypertension", Am J Physiol Heart Circ Physiol 307: H574-H586, Jun. 14, 2014.

Swanson et al., "Omega-3 Fatty Acids EPA and DHA: Health Benefits Throughout Life", American Society for Nutrition. Adv. Nutr. 3: 1-7, 2012.

POLYUNSATURATED FATTY ACID MONOGLYCERIDES, COMPOSITIONS, METHODS AND USES THEREOF

CROSS-REFERENCE TO RELATED APPLICATIONS

The present application is a continuation of U.S. patent application Ser. No. 16/517,607, filed on Jul. 21, 2019 that is a continuation-in-part of International patent application no. PCT/CA2019/050139, filed on Feb. 4, 2019, which claims priority to U.S. application No. 62/627,244 filed on Feb. 7, 2018. These documents are hereby incorporated by reference in their entirety.

FIELD OF THE DISCLOSURE

The present document relates to the field of chemical biology. More particularly, it relates to polyunsaturated fatty acid monoglyceride compounds and combinations thereof. It also provides methods for increasing the lifespan and/or slowing down the ageing process of a subject in need thereof. There is also provided a method for enhancing and/or optimizing the mitochondrial functions of a subject in need thereof by decreasing the mitochondrial proton LEAK and/or increasing the mitochondrial OXPHOS and/or increasing the COUPLING EFFICIENCY.

BACKGROUND OF THE DISCLOSURE

The normal functions of an organism gradually decline with ageing and the exact mechanism are not totally understood. One consensus upon almost all specialists is that mitochondria are involved in the ageing process (Payne, B. A. I. and P. F. Chinnery. 2015 "Mitochondrial dysfunction in aging: Much progress but many unresolved questions." Biochimica et Biophysica Acta 1847; 11: 1347-1353).

SUMMARY OF THE DISCLOSURE

According to one aspect there is provided at least one compound chosen from compound of formula (I), compound of formula (II), compound of formula (III) and compound of formula (IV):

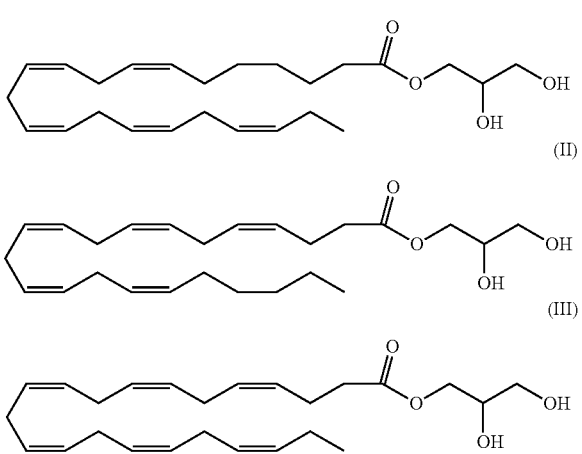

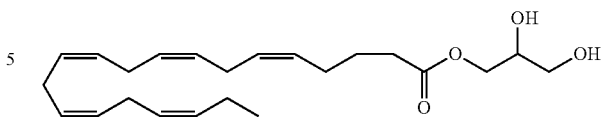

for increasing the life span of a subject in need thereof.

According to another aspect there is provided at least one compound chosen from compound of formula (I), compound of formula (II), compound of formula (III) and compound of formula (IV) for increasing of the disability-free life expectancy of a subject in need thereof.

According to another aspect there is provided at least one compound chosen from compound of formula (I), compound of formula (II), compound of formula (III) and compound of formula (IV) for slowing down the ageing process of a subject in need thereof.

According to another aspect there is provided at least one compound chosen from compound of formula (I), compound of formula (II), compound of formula (III) and compound of formula (IV) for increasing the mitochondrial OXPHOS of a subject in need thereof.

According to another aspect there is provided at least one compound chosen from compound of formula (I), compound of formula (II), compound of formula (III) and compound of formula (IV) for decreasing the mitochondrial LEAK of a subject in need thereof.

According to another aspect there is provided at least one compound chosen from compound of formula (I), compound of formula (II), compound of formula (III) and compound of formula (IV) for increasing the mitochondrial RCR or COUPLING EFFICIENCY of a subject in need thereof.

According to another aspect there is provided at least one compound chosen from compound of formula (I), compound of formula (II), compound of formula (III) and compound of formula (IV) for optimizing the mitochondrial functions of a subject in need thereof.

According to another aspect there is provided the use of at least one compound chosen from compound of formula (I), compound of formula (II), compound of formula (III) and compound of formula (IV) for increasing the life span of a subject in need thereof.

According to another aspect there is provided the use of at least one compound chosen from compound of formula (I), compound of formula (II), compound of formula (III) and compound of formula (IV) for increasing of the disability-free life expectancy of a subject in need thereof.

According to another aspect there is provided the use of at least one compound chosen from compound of formula (I), compound of formula (II), compound of formula (III) and compound of formula (IV) for slowing down the ageing process of a subject in need thereof.

According to another aspect there is provided the use of at least one compound chosen from compound of formula (I), compound of formula (II), compound of formula (III) and compound of formula (IV) for increasing the mitochondrial OXPHOS of a subject in need thereof.

According to another aspect there is provided the use of at least one compound chosen from compound of formula (I), compound of formula (II), compound of formula (III) and compound of formula (IV) for decreasing the mitochondrial LEAK of a subject in need thereof.

According to another aspect there is provided the use of at least one compound chosen from compound of formula (I), compound of formula (II), compound of formula (III) and compound of formula (IV) for increasing the mitochondrial RCR or COUPLING EFFICIENCY of a subject in need thereof.

According to another aspect there is provided the use of at least one compound chosen from compound of formula (I), compound of formula (II), compound of formula (III) and compound of formula (IV) for optimizing the mitochondrial functions of a subject in need thereof.

According to another aspect there is provided the use of at least one compound chosen from compound of formula (I), compound of formula (II), compound of formula (III) and compound of formula (IV) in the manufacture of a medicament for increasing the life span of a subject in need thereof.

According to another aspect there is provided the use of at least one compound chosen from compound of formula (I), compound of formula (II), compound of formula (III) and compound of formula (IV) in the manufacture of a medicament for increasing of the disability-free life expectancy of a subject in need thereof.

According to another aspect there is provided the use of at least one compound chosen from compound of formula (I), compound of formula (II), compound of formula (III) and compound of formula (IV) in the manufacture of a medicament for slowing down the ageing process of a subject in need thereof.

According to another aspect there is provided the use of at least one compound chosen from compound of formula (I), compound of formula (II), compound of formula (III) and compound of formula (IV) in the manufacture of a medicament for increasing the mitochondrial OXPHOS of a subject in need thereof.

According to another aspect there is provided the use of at least one compound chosen from compound of formula (I), compound of formula (II), compound of formula (III) and compound of formula (IV) in the manufacture of a medicament for decreasing the mitochondrial LEAK of a subject in need thereof.

According to another aspect there is provided the use of at least one compound chosen from compound of formula (I), compound of formula (II), compound of formula (III) and compound of formula (IV) in the manufacture of a medicament for increasing the mitochondrial RCR or COUPLING EFFICIENCY of a subject in need thereof.

According to another aspect there is provided the use of at least one compound chosen from compound of formula (I), compound of formula (II), compound of formula (III) and compound of formula (IV) in the manufacture of a medicament for optimizing the mitochondrial functions of a subject in need thereof.

According to another aspect there is provided a method for increasing the life span of a subject in need thereof comprising administering an effective amount of at least one compound chosen from compound of formula (I), compound of formula (II), compound of formula (III) and compound of formula (IV).

According to another aspect there is provided a method for increasing of the disability-free life expectancy of a subject in need thereof comprising administering to the subject an effective amount of at least one compound chosen from compound of formula (I), compound of formula (II), compound of formula (III) and compound of formula (IV).

According to another aspect there is provided a method for slowing down the ageing process of a subject in need thereof comprising administering to the subject an effective amount of at least one compound chosen from compound of formula (I), compound of formula (II), compound of formula (III) and compound of formula (IV).

According to another aspect there is provided a method for increasing the mitochondrial OXPHOS of a subject in need thereof comprising administering to the subject an effective amount of at least one compound chosen from compound of formula (I), compound of formula (II), compound of formula (III) and compound of formula (IV).

According to another aspect there is provided a method for decreasing the mitochondrial LEAK of a subject in need thereof of a subject in need thereof comprising administering to the subject an effective amount of at least one compound chosen from compound of formula (I), compound of formula (II), compound of formula (III) and compound of formula (IV).

According to another aspect there is provided a method for increasing the mitochondrial RCR or COUPLING EFFICIENCY of a subject in need thereof comprising administering to the subject an effective amount of at least one compound chosen from compound of formula (I), compound of formula (II), compound of formula (III) and compound of formula (IV).

According to another aspect there is provided a method for optimizing the mitochondrial functions of a subject in need thereof comprising administering to the subject an effective amount of at least one compound chosen from compound of formula (I), compound of formula (II), compound of formula (III) and compound of formula (IV).

According to another aspect, there is provided a composition comprising:
(i) at least one compound chosen from compound of formula (I), compound of formula (II), compound of formula (III) and compound of formula (IV);
(ii) at least one ingredient chosen from lipids, a $C_{10}$ saturated rich oils, selenium, vitamin B and cannabinoids.

According to another aspect, there is provided a composition comprising (i) at least one compound chosen from compound of formula (I), compound of formula (II), compound of formula (III) and compound of formula (IV) at compounds and (ii) at least one of a lipid and $C_{10}$ saturated rich oil for increasing the life span or the disability-free life expectancy of a subject in need thereof According to another aspect, there is provided a composition comprising (i) at least one compound chosen from compound of formula (I), compound of formula (II), compound of formula (III) and compound of formula (IV) at compounds and (ii) at least one of a lipid and selenium for increasing the life span or the disability-free life expectancy of a subject in need thereof.

According to another aspect, there is provided a composition comprising (i) at least one compound chosen from compound of formula (I), compound of formula (II), compound of formula (III) and compound of formula (IV) at compounds and (ii) at least one a lipid and vitamin B for increasing the life span or the disability-free life expectancy of a subject in need thereof.

According to another aspect, there is provided a composition comprising (i) at least one compound chosen from compound of formula (I), compound of formula (II), compound of formula (III) and compound of formula (IV) at compounds and (ii) at least one of a lipid and a cannabinoid for increasing the life span or the disability-free life expectancy of a subject in need thereof.

BRIEF DESCRIPTION OF THE FIGURES

Further features and advantages will become more readily apparent from the following description of specific embodiments as illustrated by way of examples in the appended figures wherein.

DETAILED DESCRIPTION OF THE DISCLOSURE

Figure 1:
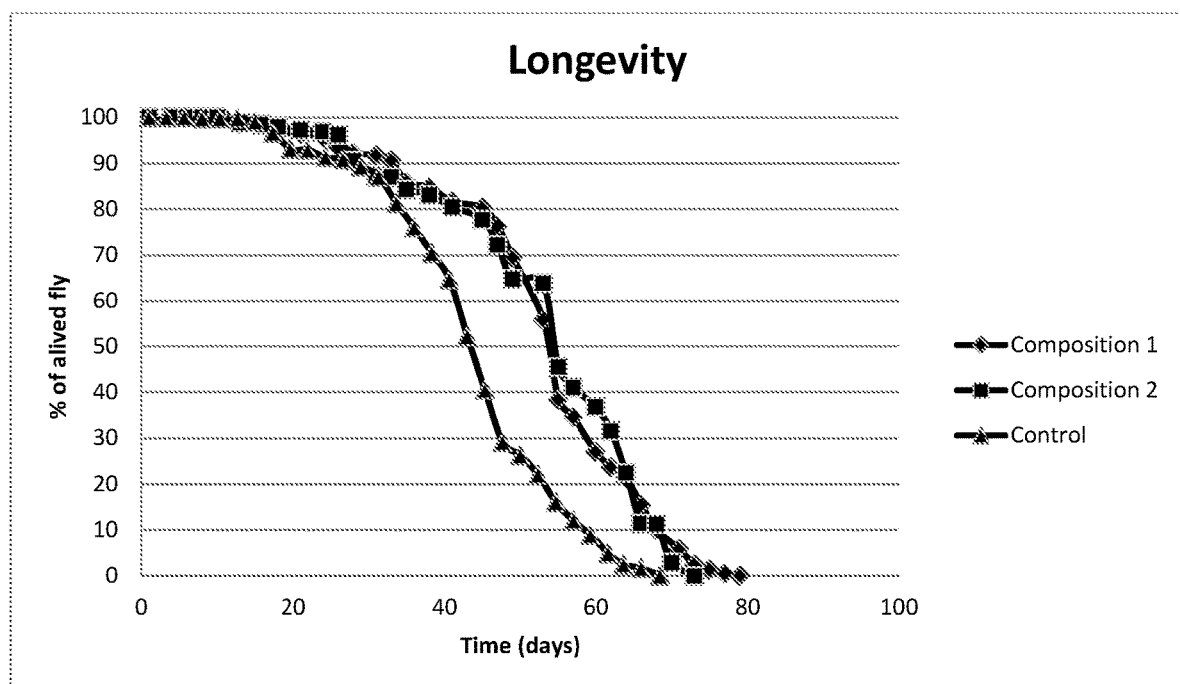
FIG. 1 represents the survival curve of *Drosophila melanogaster* males fed a standard diet (SD), a standard diet supplemented with composition 1, and a standard diet supplemented with composition 2. Results are presented as the percentage of *Drosophila* alive counted every 2-3 days (N>145 for each group).

Further features and advantages of the previously-mentioned compounds will become more readily apparent from the following description of non-limiting examples.

The term "OXPHOS" as used herein refers to oxidative phosphorylation that is the metabolic pathway in which cells use enzymes to oxidize nutrients, thereby releasing energy which is used to produce adenosine triphosphate (ATP).

The term "LEAK" as used herein refers to a leak of protons that occurs across the mitochondrial inner membranes of eukaryotic cells.

The term "RCR" or "COUPLING EFFICIENCY" or "RESPIRATORY ACCEPTOR CONTROL RATIO" as used herein refers to a value calculated by OXPHOS/LEAK or state 3/state 4.

The term "lipid" as used herein refers to as any fat-soluble (lipophilic), molecules, such as fats, fat-like substances, oils (such as animal oil, marine oil or vegetable oil), waxes, sterols (such as cholesterol, ergosterol, sitosterol, stigmasterol, fat-soluble vitamins (such as vitamins A, D, E and K), fatty acids, oxidized fatty acid (such as lipoxin, specialized pro-resolving mediators or epoxydes), fatty acids esters thereof, and various derivatives thereof such as monoglycerides, diglycerides, triglycerides, phospholipids, glycolipids, and cerebrosides and pharmaceutically acceptable salts thereof.

The term "selenium" as used herein refers to mineral form such as selenates, selenides, selenites or selenocyanate or organoselenium form such as selenols, selenonic acid, seleno amino acids or selenoproteins.

The term "vitamin B" as used herein refers to vitamin B1 (thiamine), vitamin B2 (riboflavin), vitamin B3 (niacin or nicotinamide riboside, vitamin B5 (pantothenic acid), vitamin B6 (pyridoxine, pyridoxal, pyridoxamine), vitamin B7 (biotin), vitamin B9 (folate) or vitamin B12 (cobalamins).

The term "cannabinoids" as used herein refers to THC (Tetrahydrocannabinol), THCA (Tetrahydrocannabinolic acid), CBD (Cannabidiol), CBDA (Cannabidiolic Acid), CBN (Cannabinol), CBG (Cannabigerol), CBC (Cannabichromene), CBL (Cannabicyclol), CBV (Cannabivarin), THCV (Tetrahydrocannabivarin), CBDV, (Cannabidivarin), CBCV (Cannabichromevarin), CBGV (Cannabigerovarin), CBGM, (Cannabigerol Monomethyl Ether), CBE (Cannabielsoin) or CBT (Cannabicitran).

The expression "life span" as used herein refers to Maximum life span (the maximum lifespan observed in a group), the Life expectancy (the average lifespan expected of a group) or the Longevity, (the average lifespan expected under ideal conditions).

The expression "disability-free life expectancy" as used herein refers to the Healthy Life Years (HLY) indicator (also called disability-free life expectancy) that measures the number of remaining years that a person of a certain age is still supposed to live without disability.

The expression "effective amount" of a compound of the present disclosure is a quantity sufficient to, when administered to the subject, including a mammal, for example a human, effect beneficial or desired results, including clinical results, and, as such, an "effective amount" depends upon the context in which it is being applied. The amount of a given compound of the present disclosure that will correspond to such an amount will vary depending upon various factors, such as the given drug or compound, the pharmaceutical formulation, the route of administration, the identity of the subject or host being treated, and the like, but can nevertheless be routinely determined by one skilled in the art.

For example, the subject in need thereof can be a bee, human, cat, dog, etc. . . .

For example, the at least one compound is said compound of formula (I).

For example, the at least one compound is said compound of formula (II).

For example, the at least one compound is said compound of formula (III).

For example, the at least one compound is said compound of formula (IV).

For example, the at least one compound is said compound of formula (I), said compound of formula (III) and said compound of formula (IV).

For example, the at least one compound is said compound of formula (I) and said compound of formula (IV).

For example, the at least one compound is said compound of formula (I) and said compound of formula (III).

For example, the at least one compound is said compound of formula (III) and said compound of formula (IV).

For example, the at least one compound can be for use in combination with at least one ingredient chosen from lipids, a $C_{10}$ saturated rich oils, selenium, vitamin B and cannabinoids.

For example, the at least one ingredient and said at least one compound can be for simultaneous administration.

For example, the at least one ingredient and said at least one compound can be for separate administration.

For example, the at least one compound chosen from compound of formula (I), compound of formula (II), compound of formula (III) and compound of formula (IV) can be administered in combination with at least one ingredient chosen from lipids, a $C_{10}$ saturated rich oils, selenium, vitamin B and cannabinoids.

For example, the at least one ingredient and said at least one compound can be administered simultaneously.

For example, the at least one ingredient and said at least one compound can be administered separately.

Further features and advantages of the previously-mentioned compounds will become more readily apparent from the following description of non-limiting examples.

EXAMPLE 1

Preparation of a Composition (Composition 1) Comprising Compound III.

Composition 1 comprising compound IV, was prepared by reacting 1 kg of EPA concentrated fish oil (ethyl ester form) with 0.27 kg of glycerol with 0.05 kg of Novozym 435 (lipase) in 2 kg of acetone at 50° C. for 4 h. The lipase was filtered, the acetone was removed in vacuo and the mixture was allowed to stand for phase separation. The lower unreacted glycerol phase was removed to give 1 kg of the final composition 1 comprising compound IV, unreacted ethyl ester and small amount of diglycerides and triglyceride.

EXAMPLE 2

Preparation of a Composition (Composition 2) Comprising Compound II.

Composition 2 comprising compound III, was prepared by reacting 1 kg of DHA concentrated fish oil (ethyl ester form) with 0.27 kg of glycerol with 0.05 kg of Novozym 435 (lipase) in 2 kg of acetone at 50° C. for 4 h. The lipase was filtered, the acetone was removed in vacuo and the mixture was allowed to stand for phase separation. The lower unreacted glycerol phase was removed to give 1 kg of the final composition 2 comprising compound III, unreacted ethyl ester and small amount of diglycerides and triglyceride.

EXAMPLE 3

Figure 2:
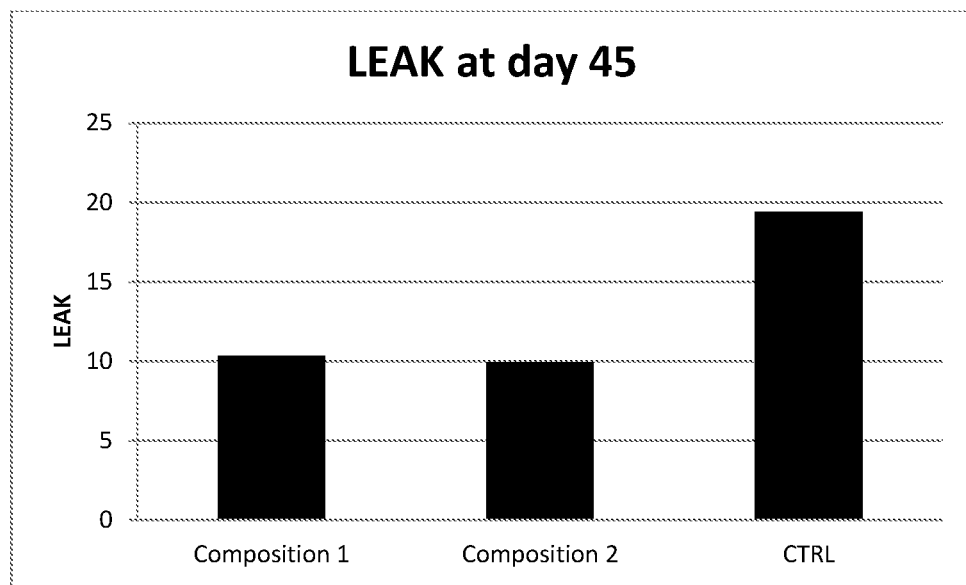
FIG. 2 represents the effects of composition 1 and composition 2 on mass-specific mitochondrial LEAK of thorax muscle from *Drosophila melanogaster* at day 45.
Figure 3:
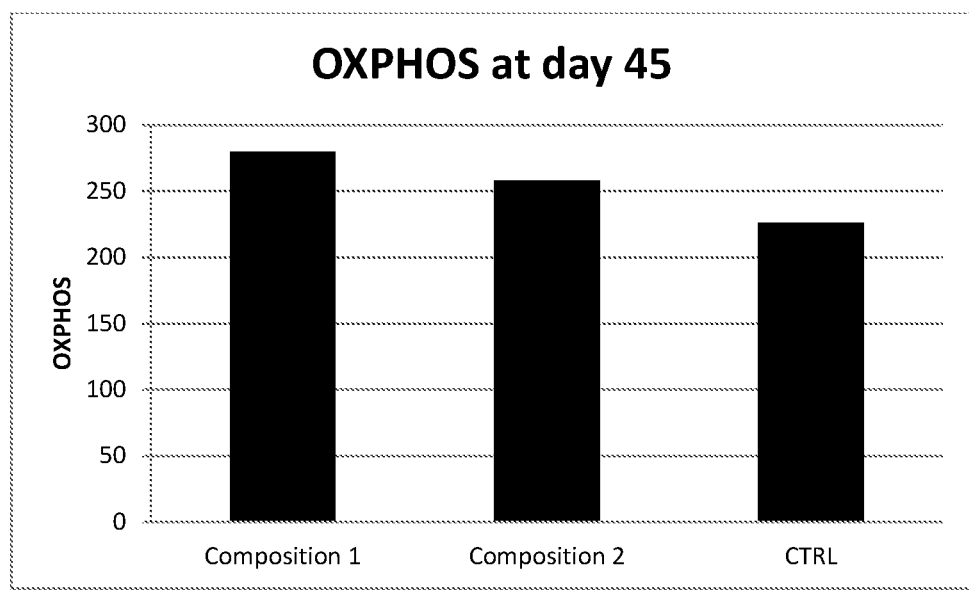
FIG. 3 represents the effects of composition 1 and composition 2 on mass-specific mitochondrial OXPHOS of thorax muscle from *Drosophila melanogaster* at day 45.

Composition 1 and Composition 2 Extend Longevity in D. Melanogaster by Decreasing the LEAK, Increasing the OXPHOS and Increasing
Coupling Efficiency Male Drosophila (strain w1118, Bloomington Drosophila Stock Center, Bloomington, Ind., USA) were collected on the day of hatching and were fed a standard cornmeal diet (SD), or a SD supplemented with 0.3 mg·mL-1 of a formulation containing composition 1 or composition 2. The longevity is presented in FIG. 1 and was evaluated by recording the survival of flies every 2-3 days (N>145, in triplicates). The three groups were significantly different from each other (log-rank $\chi2$=16.5, P<0.001 between SD and composition 2; log-rank $\chi2$=48.3, P<0.001 between SD and composition 1; log-rank $\chi2$=9.8, P=0.002 between composition 2 and composition 1). Specifically, median lifespans were similar between composition 2 and composition 1 (55 days) and both were higher than when the flies were fed the SD (48 days). Maximal lifespan was however the highest with composition 1 (79 days), followed by composition 2 (73 days) and SD (68.5 days). Mitochondrial oxygen consumption was evaluated in permeabilized thorax of Drosophila at 45 days old, N=5-6 for each dietary treatment. LEAK of Drosophila fed either composition 1 or composition 2 were lower than with the SD, FIG. 2. Moreover, flies fed composition 1 presented higher OXPHOS than SD FIG. 3.

Figure 4:
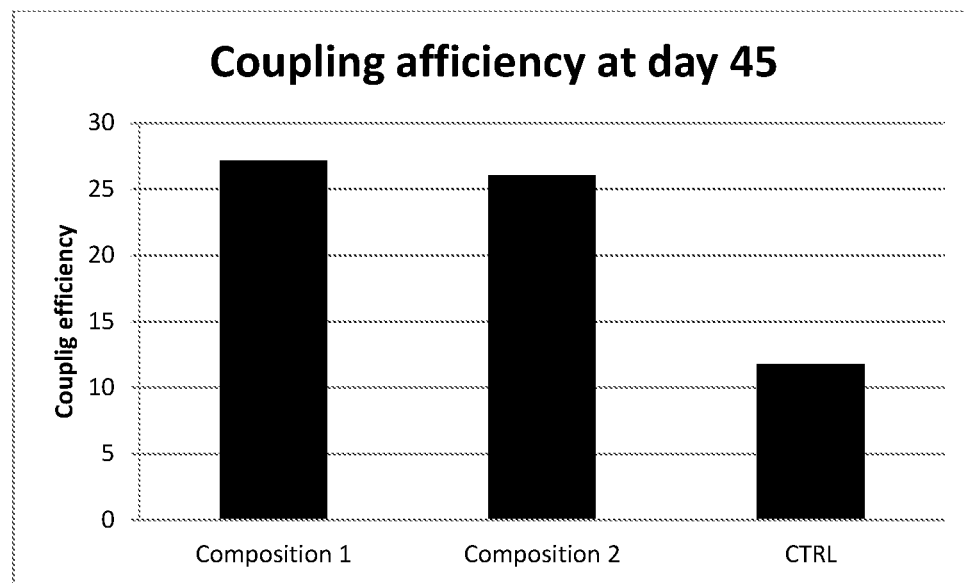
FIG. 4 represents the effects of composition 1 and composition 2 on mass-specific mitochondrial COUPLING EFFICIENCY of thorax muscle from *Drosophila melanogaster* at day 45.

Both composition 1 and composition 2 also had higher COUPLING EFFICIENCY than SD, and composition 1 presented higher COUPLING EFFICIENCY than composition 2 FIG. 4)

EXAMPLE 4

Composition 1 Decreases Mitochondrial Proton Leak, Increase the OXPHOS and Ameliorate the COUPLING EFFICIENCY in a Pilot Human Clinical Trial.

Figure 5:
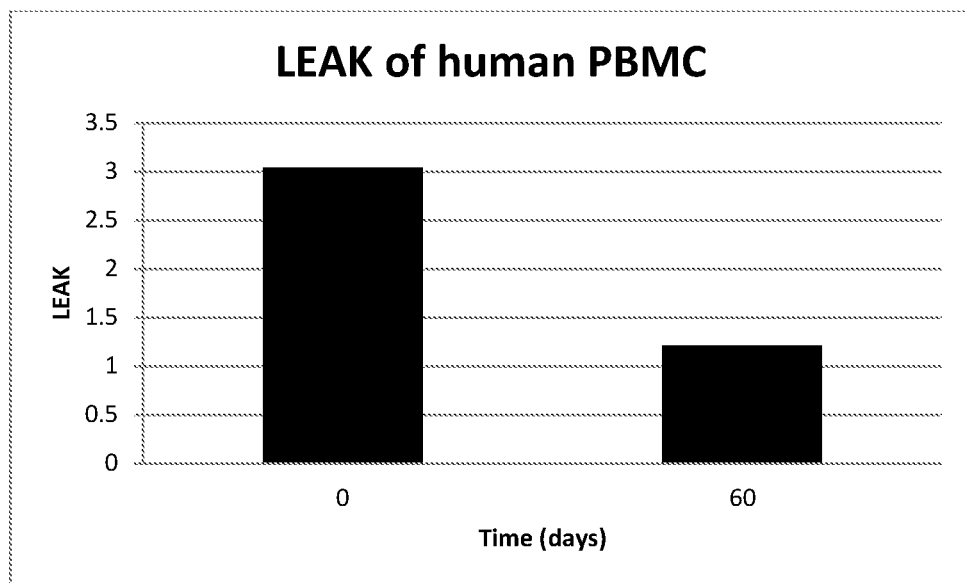
FIG. 5 represents the variation of the LEAK of the PBMC at T=0 and T=60 days.
Figure 6:
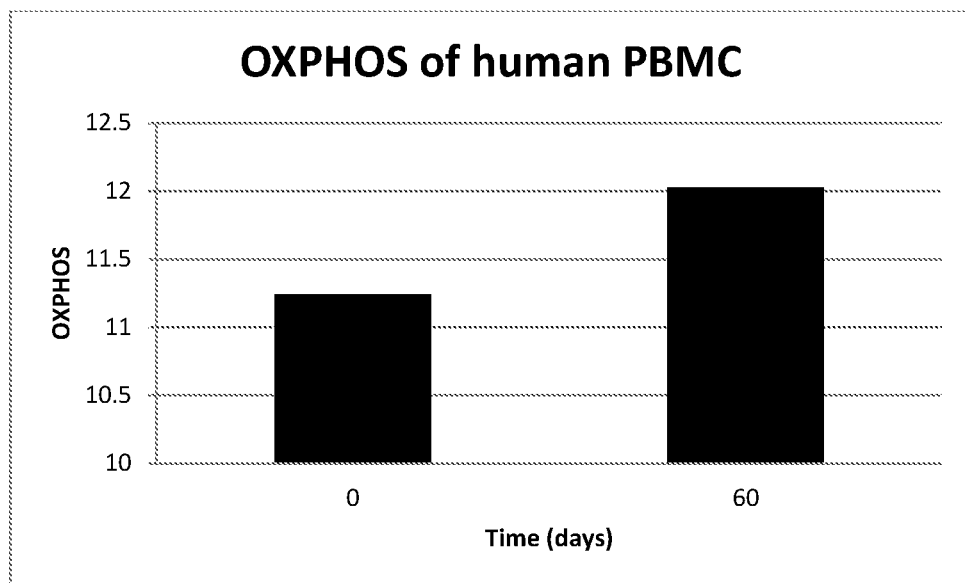
FIG. 6 represents the variation of the OXPHOS of the PBMC at T=0 and T=60 days.
Figure 7:
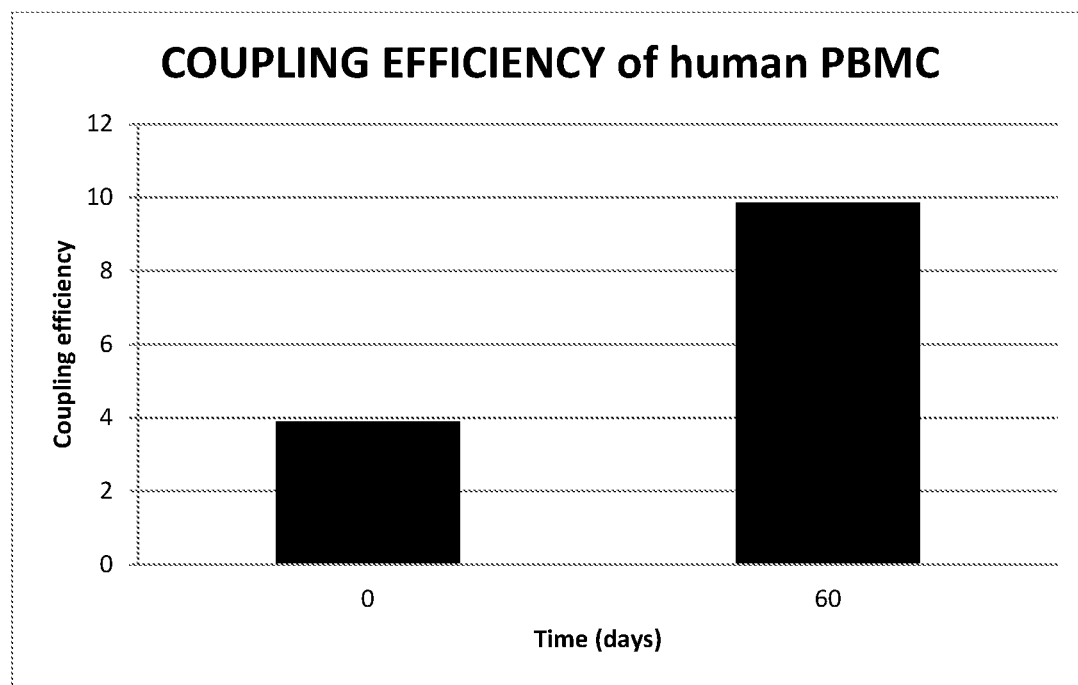
FIG. 7 represents the variation of the COUPLING EFFICIENCY of the PBMC at T=0 and T=60 days.

Four patients were recruited at SCF Pharma and the study was approved by a review boards. Prior to participation, all subjects signed a written informed consent form previously reviewed and discussed with a study investigator. Eligible subjects received composition 1 (1.5 g) for 60 days. The mean LEAK of the PBMC cells of the patients at T=0 (3.04) and T=60 days (1.21) is presented in FIG. 5, the mean OXPHOS of the PBMC cells of the patients at T=0 (11.24) and T=60 days (12.03) is presented in FIG. 6, and the mean COUPLING EFFICIENCY of the PBMC cells of the patients at T=0 (3.89) and T=60 days (9.86) is presented in FIG. 7

While the compounds, compositions, methods and uses thereof have been described in connection with specific embodiments thereof, it will be understood that they can be further modified and this application is intended to cover any variations, uses, or adaptations of the compounds, compositions, methods and uses thereof following, in general, the principles described in the present document and including such departures from the present disclosure as come within known or customary practice within the art to which the present document pertains and as may be applied to the features hereinbefore set forth, and as follows in the scope of the appended claims.

EXAMPLE 5

Composition 1 Decreases Mitochondrial Proton Leak, Increase the OXPHOS and Ameliorate the COUPLING EFFICIENCY in a Second Pilot Human Clinical Trial.

Figure 8:
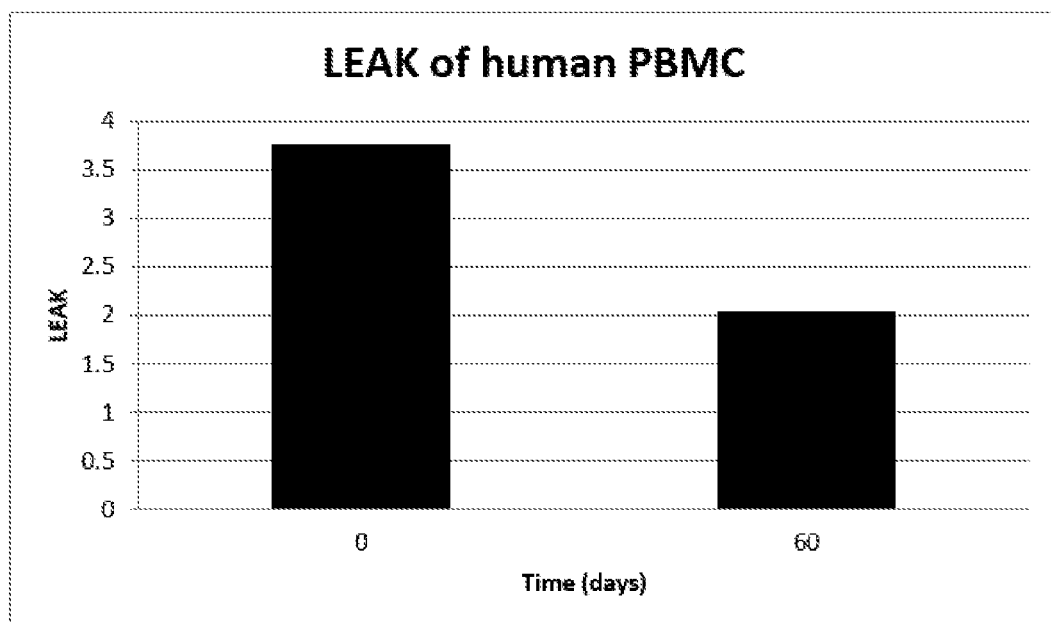
FIG. 8 represents the variation of the LEAK of the PBMC at T=0 and T=60 days.
Figure 9:
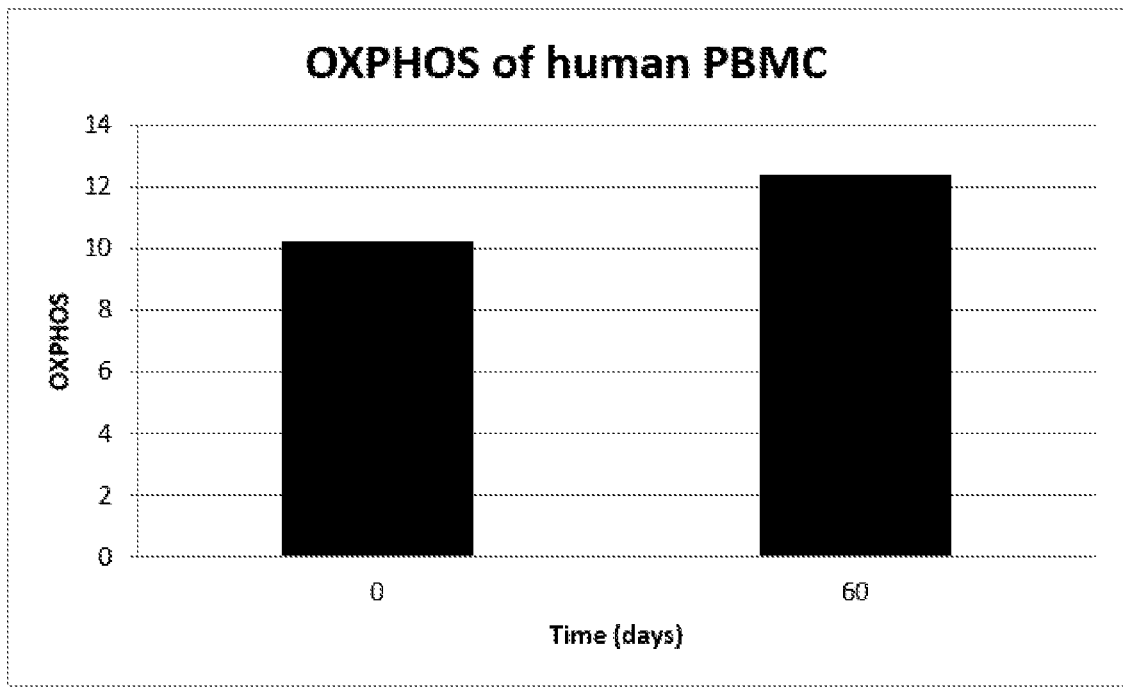
FIG. 9 represents the variation of the OXPHOS of the PBMC at T=0 and T=60 days.
Figure 10:
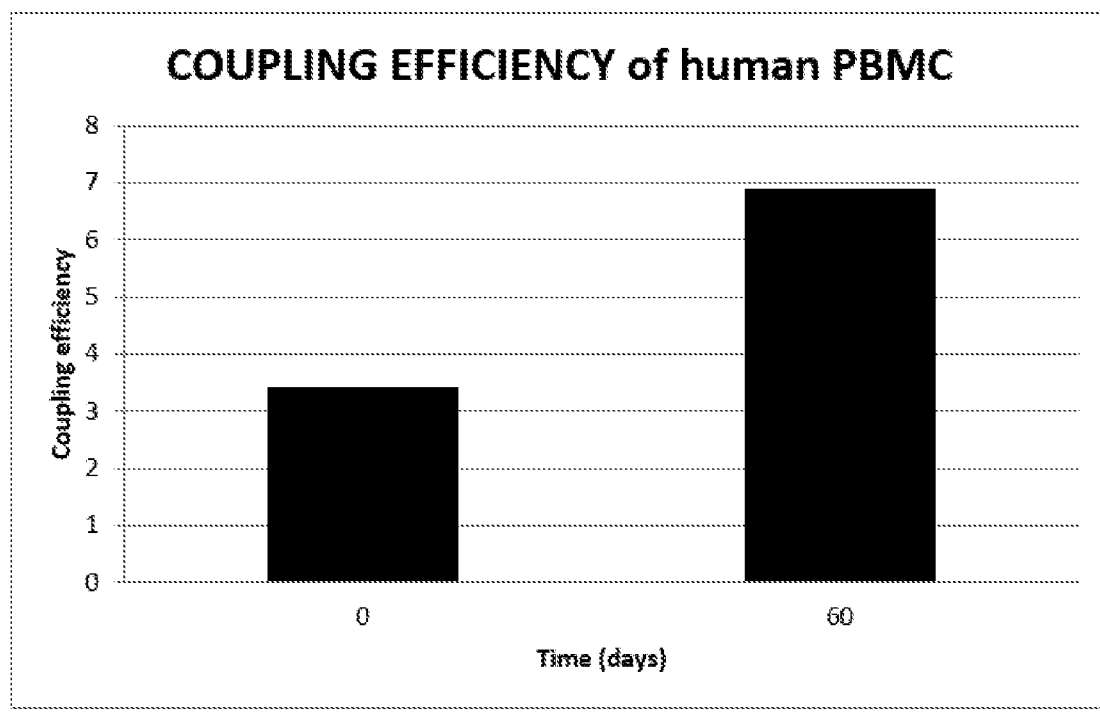
FIG. 10 represents the variation of the COUPLING EFFICIENCY of the PBMC at T=0 and T=60 days.

Six patients were recruited at SCF Pharma and the study was approved by a review boards. Prior to participation, all subjects signed a written informed consent form previously reviewed and discussed with a study investigator. Eligible subjects received composition 1 (1.5 g) for 60 days. The mean LEAK of the PBMC cells of the patients at T=0 (3.76) and T=60 days (2.04) is presented in FIG. 8, the mean OXPHOS of the PBMC cells of the patients at T=0 (10.24) and T=60 days (12.40) is presented in FIG. 9, and the mean COUPLING EFFICIENCY of the PBMC cells of the patients at T=0 (3.42) and T=60 days (6.89) is presented in FIG. 10.

EXAMPLE 6

Figure 11:
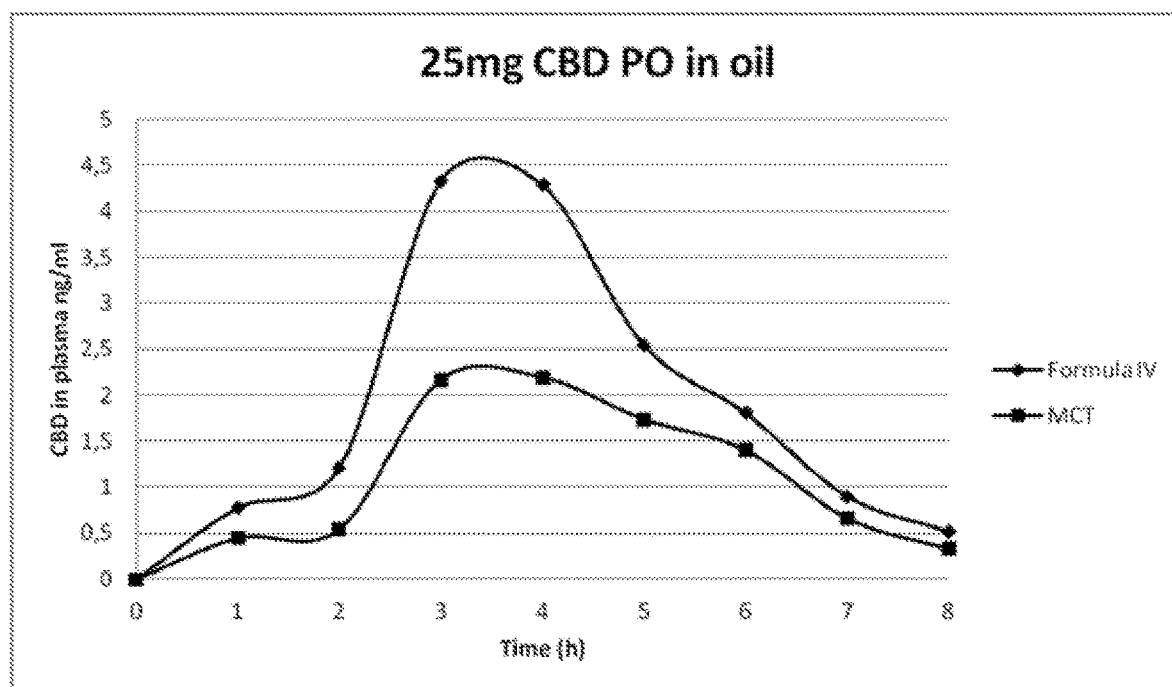
FIG. 11 shows the superiority of the compound of formula (IV) over the MCT oil on the absorption and bioavailability of CBD.

54 mg of cannabidiol (CBD) was dissolved in 2.5 g of compound of formula (IV) to give a clear solution. 1.16 g of the mixture (25 mg CBD) was encapsulated in two (2) hard gel capsules (size 00) for absorption study. A pilot absorption study was conducted in one volunteer. The two (2) hard gel capsules were swallowed with a glass of water by the volunteer fasted for 10 h. 200 ul of blood was collected by a lancet in a heparinised microtube at T=0, 1, 2, 3, 4, 5, 6, 7 and 8 h. The plasma was analyzed by HPLC/MS/MS to quantify the CBD. A comparative study was conducted with the same amount of CBD but with MCT oil (medium-chain triglycerides oil) instead of compound of formula (IV). FIG. 11 shows the superiority of the compound of formula (IV) over the MCT oil on the absorption and bioavailability of CBD.

EXAMPLE 7

Figure 12:
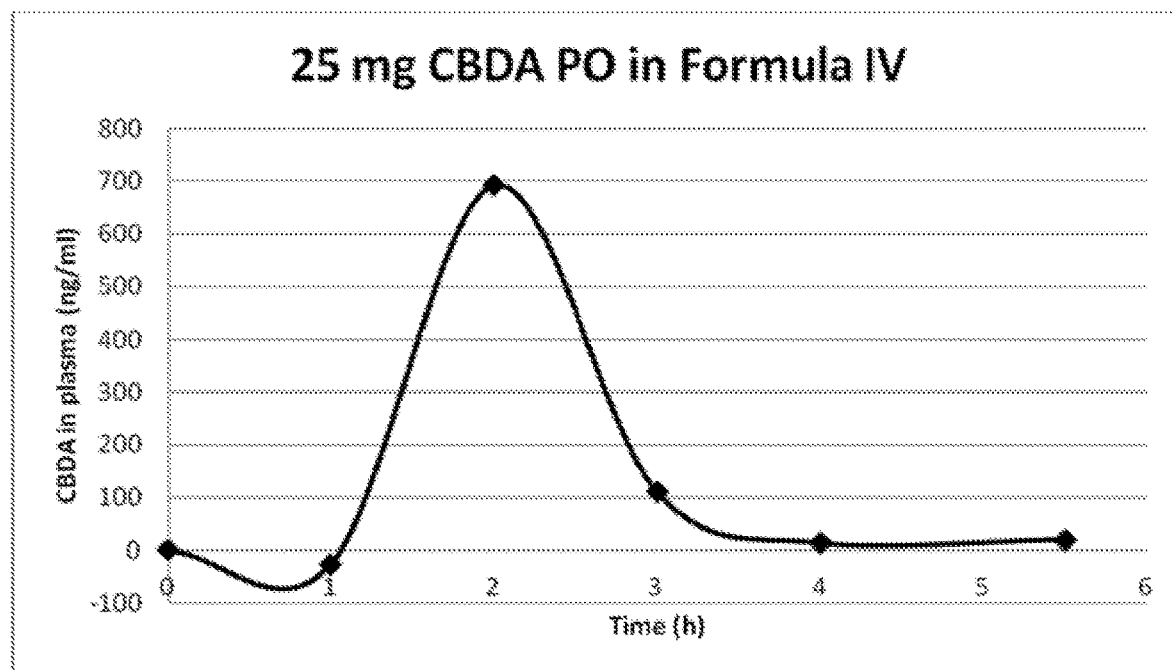
FIG. 12 shows the absorption and bioavailability profile of CBDA in plasma.

166 mg of cannabidiolic acid (CBDA) crude extract containing 20% CBDA was dissolved in 1.33 g of compound of formula (IV) to give a clear solution. 1.00 g of the mixture (25 mg CBDA) was encapsulated in two (2) hard gel capsules (size 00) for absorption study. A pilot absorption study was conducted in one volunteer. The two (2) hard gel capsules were swallowed with a glass of water by the volunteer fasted for 10 h. 200 ul of blood was collected by a lancet in a heparinised microtube at T=0, 1, 2, 3, 4, 5, 6, 7 and 8 h. The plasma was analyzed by HPLC/MS/MS to quantify the CBDA. FIG. 12 shows the absorption and bioavailability profile of CBDA in plasma.

EXAMPLE 8

Figure 13:
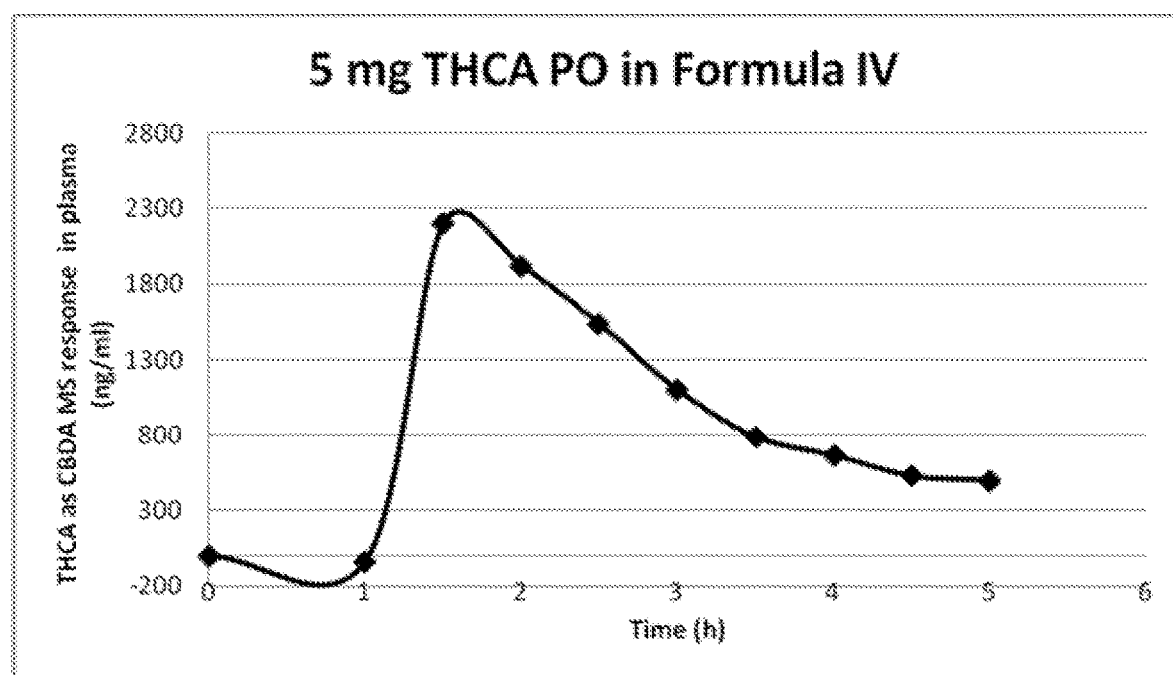
FIG. 13 shows the absorption and bioavailability profile of THCA in plasma.

106 mg of tetrahydrocannabinolic acid (THCA) crude extract containing 20% THCA was dissolved in 4.00 g of compound of formula (IV) to give a clear solution. 1.00 g of the mixture (5 mg THCA) was encapsulated in two (2) hard gel capsules (size 00) for absorption study. A pilot absorption study was conducted in one volunteer. The two (2) hard gel capsules were swallowed with a glass of water by the volunteer fasted for 10 h. 200 ul of blood was collected by a lancet in a heparinised microtube at T=0, 1, 2, 3, 4, 5, 6, 7 and 8 h. The plasma was analyzed by HPLC/MS/MS to quantify the THCA (the calibration curve was made with CBDA). FIG. 13 shows the absorption and bioavailability profile of THCA in plasma.

While the compounds, compositions, methods and uses thereof have been described in connection with specific embodiments thereof, it will be understood that they can be further modified and this application is intended to cover any variations, uses, or adaptations of the compounds, compositions, methods and uses thereof following, in general, the principles described in the present document and including such departures from the present disclosure as come within known or customary practice within the art to which the present document pertains and as may be applied to the features hereinbefore set forth, and as follows in the scope of the appended claims.

What is claimed is:

1. A composition consisting essentially of synthetic SN1 monoglyceride of fish oil, a synthetic diglyceride of fish oil selected from the group consisting of SN 1,2 synthetic diglyceride and SN 1,3 synthetic diglyceride, isolated cannabidiol, synthetic ethyl ester of fish oil and glycerol.

* * * * *